United States Patent [19]

Carter

[11] Patent Number: 4,945,082

[45] Date of Patent: Jul. 31, 1990

[54] CONTROLLED DSRNA THERAPY FOR HUMAN VIRAL INFECTIONS

[75] Inventor: William A. Carter, Birchrunville, Pa.

[73] Assignee: HEM Research, Inc., Rockville, Md.

[21] Appl. No.: 167,190

[22] Filed: Mar. 11, 1988

Related U.S. Application Data

[63] Continuation-in-part of Ser. No. 136,978, Dec. 23, 1987, which is a continuation-in-part of Ser. No. 900,614, Aug. 26, 1986, Pat. No. 4,795,744, which is a continuation-in-part of Ser. No. 886,363, Jul. 17, 1986, abandoned, which is a continuation-in-part of Ser. No. 769,494, Aug. 26, 1985, abandoned.

[51] Int. Cl.$^5$ .............................................. A61K 31/70
[52] U.S. Cl. ...................................... 514/44; 514/935
[58] Field of Search ........................... 514/44, 49, 935; 424/85.1–85.7

[56] References Cited

U.S. PATENT DOCUMENTS 4,795,744  1/1989  Cater ...................................... 514/44

Primary Examiner—John W. Rollins
Attorney, Agent, or Firm—Nixon & Vanderhye

[57] ABSTRACT

The rate of viral dysfunction of subject's immune response in the rate of progression of HIV or like virus from seropositive LAS Pre-ARC ARC frank AIDS is tracked and antiviral therapy based upon dsRNA is initiated and regulated using clinical measurements of the most severe immune deficit as a therapeutic indicator.

9 Claims, 1 Drawing Sheet

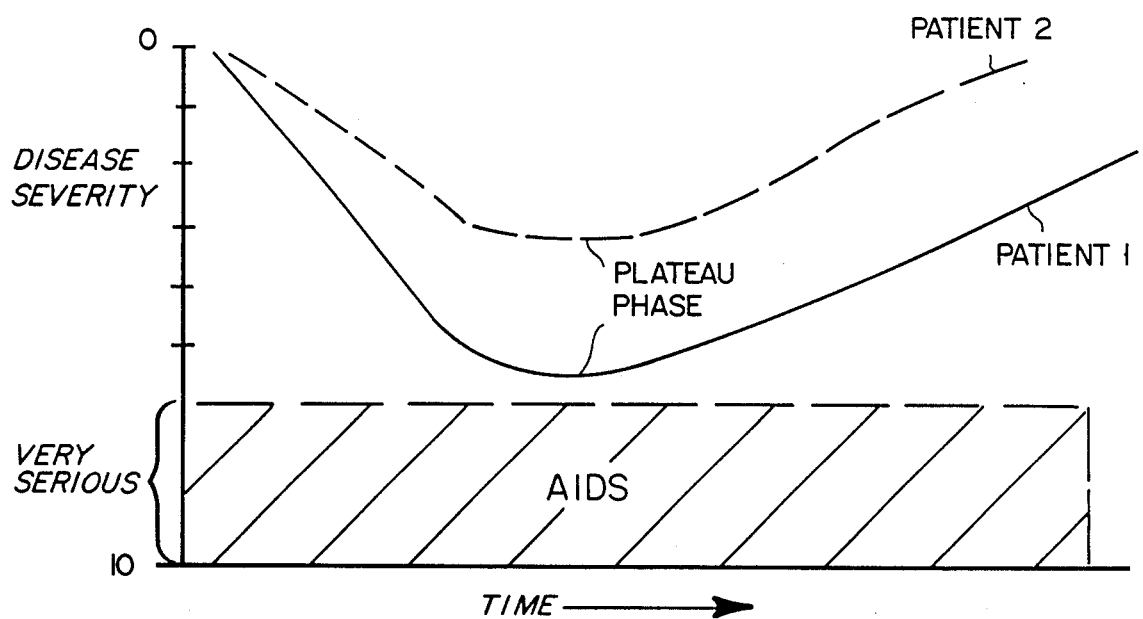

CONTROLLED DSRNA THERAPY FOR HUMAN VIRAL INFECTIONS

CROSS-REFERENCE TO RELATED APPLICATIONS

This is a continuation-in-part of my earlier application Ser. No. 136,978, filed Dec. 23, 1987, which, in turn, is a continuation-in-part of application Ser. No. 900,614 filed Aug. 26, 1986, now U.S. Pat. No. 4,795,744, which, in turn, is a continuation-in-part of application Ser. No. 886,363 filed July 17, 1986, now abandoned which, in turn, is a continuation-in-part of application Ser. No. 769,494 filed Aug. 26, 1985, now abandoned.

This invention relates to the treatment of retrovirus infections and more particularly to the treatment of human immunodeficiency virus or HIV infections and therapies for susceptible viral infections other than HIV which have a a common mechanism of viral multiplication/pathogenesis, in whole or in part, and accordingly are sensitive to the regimen of therapy employed.

BACKGROUND OF THE INVENTION

Acquired Immunity Syndrome or AIDS appears to be a progressive disease, although the rate of transition from one phase to another can be variable. These phases have assigned classifications. Asymptomatic individuals infected by HIV exist, as judged by the presence of circulating antibodies against the virus (M. G. Sarngadharan et al, *Science*, volume 224, p. 506, 1984). If they have no other markers, they are WR1 stage patients, by the Walter Reed classification (R. R. Redfield et al, *New England Journal of Medicine*, volume 314, p. 131, 1986). They have been also called pre ARC (ARC=AIDS-related complex), although some of these individuals may never develop ARC symptomatology. Some of these patients may develop lymphadenopathy (WR2) and exhibit the T4 cell deficit (WR3). Next, the ability of lymphocytes to undergo antigen-stimulated proliferation and antigen-stimulated interferon-gamma production decreases and these WR4 patients begin to lose delayed cutaneous hypersensitivity. WR5 patients are usually anergic. They exhibit Herpes Zoster infections, oral candidiasis (thrush), or ARC symptoms which include prolonged fevers, night sweats, fatigue, diarrhea and/or weight loss. This period of ARC is usually also characterized by progressive immune decay. Finally, WR6 individuals experience opportunistic infections constituting "full-blown" AIDS, with 50% of the patients dyeing within 12 months (H. W. Murray et al, *New England Journal of Medicine*, volume 310, p. 883, 1984).

HIV infections follow a progression of symptoms and clinically measurable indicators. The infection typically progresses at a rate that is readily quantified by various available measurable disease parameters, explained in more detail below. This invention measures two or more of these parameters and correlates them with disease severity. Therapeutic intervention with dsRNAs stabilizes and reverses the otherwise inevitable downward trend of the infection.

In overall terms, there are two major stages of HIV infection —the first may be called non-life threatening and include, in order of progression: asymptomatic individuals who react positively to tests for HIV antibodies in the individuals blood or blood fraction, that is having circulating anti-HIV antibodies (the seropositive individuals); those individuals exhibiting lymphadenopathy syndrome (LAS) including symptoms of anergy or symptomless; pre-AIDS related complex (Pre ARC); and AIDS-related complex (ARC) including one or more symptoms of a generalized lymphadenopathy, fatigue, night sweats and anergy, among others. The second stage may be termed life-threatening and this is "full blown" or frank AIDS. These two major stages are depicted graphically in the attached drawing.

DETAILED DESCRIPTION OF THE INVENTION

This invention provides the clinician with a means to select a dsRNA regimen that is effective to at least delay or hopefully prevent the individual's transition from non-life threatening to life threatening HIV infection and, where possible, to reverse this otherwise inevitable progression and restore one or more individual's immune faculties. While this invention is described with emphasis on HIV infections, the causitive virus is constantly changing and appearing with slightly different characteristics. This invention also includes a regimen of diagnosis, monitoring and therapeutic intervention for susceptible viral conditions other than HIV which have a common mechanism of viral multiplication/pathogenesis, in whole or in part, and accordingly are sensitive to the diagnosis and therapy employed.

Currently available HIV treatment modialities, namely AZT (zidovudine, Retrovir®, Burroughs Wellcome Co.), are capable of prolonging the life of individuals with frank AIDS only under certain conditions. At present it is unclear whether AZT itself or AZT plus another active moiety is responsible for the product's qualified effectiveness in frank AIDS patients. Whether AZT or similar compounds will prevent or delay transition from the non-life threatening to life threatening (frank AIDS) conditions is not presently known.

I have found that careful range-finding, patient assessment and, interactive with these, judicious administration of dsRNAs, alone or in combination with other antiviral agents, delays or prevents this otherwise inevitable progression in a safe and highly-effective manner.

I have determined, following statistical analysis of over 400 HIV-infected individuals, that the rate of HIV progression from seropositive to LAS to Pre-ARC to ARC to frank AIDS differs from individual to individual, and that this rate is a function of the rate of viral dysfunction of critical components of the host response to the virus. In this procedure, various patient parameters capable of being accurately identified or quantified are correlated with HIV disease severity. These critical factors provide convenient means to assess the HIV disease progression and are readily clinically measurable immune deficits. They include:

1. Derangements in helper-induced T-lymphocytes, specifically the number of T4 cells per mm$^3$, and the ratio of T4 cells to T8 cells.
2. Delayed hypersensitivity response or skin sensitivity response to one or more skin-test antigens such as mumps, candida and trichophyton. Skin sensitivity is a convenient summation of the immune system's response to an antigen.
3. Virus load.
4. The effect of HIV on the 2', 5'-A RNase L pathway, all as described in Carter et al, *The Lancet*. p. 1286–1292 (June 6, 1987).

My studies indicate HIV may destroy or seriously damage one or more of these limbs of the immune system and that, quite surprisingly, dsRNA therapy corrects that disease parameter most adversely affected by the HIV infection. Reduction in these measurable parameters may be plotted in the manner of FIG. 1 in which the level of the patient's deterioration is a function of the slope of the downward curve.

It is important, if not essential, to treat the patient and correct the deterioration of his/her most seriously deteriorated immune parameter by appropriate patient assessment and, interactive with these, the judicious administration of dsRNAs. Correction of the most seriously deteriorated parameter is sufficient to achieve a subjective improvement in the patient; conversely, it is insufficient to correct the least deteriorated parameter, otherwise full-blown AIDS will inevitably develop.

Described is a regimen of dsRNA therapy that provides protection from development of an existing HIV infection to full-blown (and fatal) AIDS which allows gradual rebuilding of various essential immune system components, selectively to that immune system component most affected by the virus, of the immune/antiviral system at a rate which is at least equal to and usually greater than the rate of disease processes which collectively cause advancement of the disease to AIDS. Such disease processes include:

(a) flattening or reversing the downward slope of T4 cells;

(b) flattening or reversing the downward slope in skin resistivity to foreign test antigens such as mumps, candida, trichophyton, TB, and the like;

(c) flattening or reversing the increase the virus concentration in the blood and other biological fluids and cells as measured by viral antigens (p24, etc.) and viral co-culture determinations.

To accomplish these and other objectives of this invention and to find an effications dsRNA concentration (excessive concentrations are not toxic, but detract from a favorable clinical outcome) it is desirable to preform several measurements of one or more of these clinically measurable indicators of immune/antiviral activity, such as T4 cells, skin sensitivity tests, viral load, etc., as explained in more detail below. Over time, this allows one to determine the relative rate of propensity of disease progression in an individual at risk, and then to adjust the dosage and frequency of administration of dsRNA accordingly, such that the ultimate dread effect—development of full-blown AIDS—can be avoided or the incidence rate of AIDS development dramatically reduced in a population group at risk.

P24 measurement

The P24 measurement is a quantitative, immune assay for the HIV-1 (human immunodeficiency virus) viral coat protein identified as P24 (the viral molecular weight=approximately 24,000). Biological fluids, specifically blood plasma, are exposed to well-charcterized antibodies specific for the HIV viral coat protein. Antibody:Antigen complexes are captured and quantitated using an enzyme immunoassay (EIA). The test is unique in that it accurately and rapidly quantitates the presence of viral components directly as opposed to other viral tests which quantitate either the response of the immune system to an earlier viral challenge (the antibody serology assays) or the ability of biological fluids to initiate viral replication (viral culture assays). The test has been used for numerous prospective studies of AIDS and ARC. Paul et al, *J. Med. Virol.*, Aug. 1987 22 (4) 357–63.

T4 measurement

The human immunodeficiency virus specifically attacks a subset of human lymphocytes identified as T4 lymphocytes. These cells are identified both by the virus and the clinician by the presence of a specific surface protein identified as the CD4 receptor protein. The depletion of this class of lymphocytes is indicative of HIV viral replication. T4 depletion is determined by isolating patient lymphocytes and binding to them well-characterized indicator-antibodies specific for the CD4 protein. These indicator molecules have fluorescent labels. The T4 count is obtained by passing the lymphocyte:indicator-antibody complexes through a fluorescent cell counter, which individually identifies cells bound to fluorescent indicator molecules and quantitates them.

T4/T8 ratio

The T4 lymphocyte cells (identified as "helper" lymphocytes) and the T8 lymphocyte (identified as "suppressor" lymphocytes) can be identified and quantitated using specific monoclonal antibodies (see above). The ratio between helper and supressor T cells, normally 2:1, may be characteristically altered in certain disorders and provide diagnostic information. See Littman, *Annu Rev Immunol* 1987;5:561–84; and Broder *Prog Allergy* 1986;37:224–43.

Skin Test

The delayed hypersensitivity skin test determines the ability of the cell mediated immune system to respond to an antigen to which it had previously been exposed. A small quantity (0.5 ml) of commercially prepared mumps antigen, Candida antigen (1:100) and fluid tetanus toxoid (1:10) is subdermally injected. Nearly all adults and most immunized children will react to one or more of these antigens with erythema (reddening of the skin) or induration (a thickening of the skin $>$=mm in diameter) at 48 hours. Anergy, the absence of a delayed skin test response, is common in T4-related immunodeficiencies; see Sears et al, *Clin. Immunol. Immunopathol.*, Nov. 1987 45(2):177–83 and Rouvelex, *Clin. Exp. Immunol.*, Dec. 1986 66(3)574–81.

DESCRIPTION OF THE DRAWINGS

HIV infection, symptomology, disease severity and therapeutic intervention are illustrated, in the attached FIGURE.

The ordinate is degree of disease severity assessed by the parameters discussed above and illustrated in the FIGURE in arbitrary units from 0 to 10. There is no baseline; however, the asymptomatic seropositive carrier individual will exhibit little or no disease impairment assessed by these tests. AIDS, in which death is inevitable in the short term, is represented in the lower hatched zone of the graph where the disease is very severe.

As the HIV infection continues over time, represented as the abscissa (units not indicated), disease symptoms and immunological parameters decline, and as this occurs, therapeutic intervention in the form of dsRNA therapy is begun. The illustrations are given representing a composite of numerous clinical experiences (underlying data not shown). In the first illustration (indicated by the solid line) the patient has a rapid downhill course, as indicated by the slope of the downward line, and requires 600 mg/ml of blood of Ampligen three times per week. In time, a plateau is reached and after that disease severity is gradually reduced. The disease severity in the second patient (broken line) is less severe requiring only 50 mg/ml of blood of Ampligen (resulting from a 100 mg IV dose infused over a period of 30 minutes) twice a week.

Response to successful dsRNA therapy is characterized by at least two phases, as illustrated in the FIGURE. They are (A) stabilization of disease parameters, as determined by viral concentration or "load" and stabilization of immune cell deterioration, as indicated by the plateau phase, and (B) correction of the above concurrently related lesions at a rate which is faster than the rate of viral-induced pathology on one or more bodily functions. This recovery must be at a rate which is faster than viral ability to attack T4 cells or cause Kaposi's sarcoma or cause and/or allow opportunistic infections which at times in different patients may behave as non-coordinated viral functions.

From these parameters and with this explanation, it will be apparent that the moment at which therapeutic intervention occurs determines the extent and length of therapy required. The degree of maintenance versus weaning from the drug depends in substantial part on the time that treatment of the disease process is initiated. Experience to date indicates a minimum maintenance dosage of the dsRNA is required to mediate and arrest HIV development.

In the clinical environment, the dsRNA administration must be adjusted to address the rate of decay of the most critical, i.e., closest to frank AIDS, clinically measurable immune deficit assessed. Examples are: T4 cells less than 400–800/ml, HIV antigen level 2,000–10,000 mcg/ml, and absence of skin test sensitivity to antigens, anergy.

This invention includes the use of dsRNA alone or with other therapeutic antiviral agents to correct the patient's immune deficit(s) at a time in the disease progression and in an amount to at least arrest the downward progression of the disease. Mismatched double-stranded RNA, the preferred class of dsRNAs, is a known form of macromolecular RNA (see U.S. Pat. No. 4,024,222 and U.S. Pat. No. 4,130,641) in which destabilization of the double helix prevents base pairing. Mismatched dsRNA is well known for its interferon-induction properties which indicate a mechanism unrelated to interferon induction per se.

A typical therapeutic embodiment of mismatched double-stranded RNA is the synthetic dsRNA formed by complexes of polyriboinosinic and polyribocytidylic/uridylic acid, such as $rI_n \cdot r(C_x, U \text{ or } G)_n$ where x has a value from 4 to 29, e.g., $rI_n \cdot r(C_{12}U)_n$ herein referred to as Ampligen ®, a registered trademark of HEM Research, Inc., of Rockville, Md., U.S.A. Many mismatched dsRNA polymers which behave similarly to Ampligen have been studied. The key therapeutic advantage of mismatched dsRNAs over other forms of natural and/or synthetic dsRNAs is their reduced toxicity in animals and man. For example, Lampson et al in U.S. Pat. No. 3,666,646 described earlier complexes of dsRNA which are capable of triggering various interferon-related effects, but the toxicity of such compounds precluded any clinical utility in the treatment of cancer or related disorders.

By "mismatched dsRNA" are meant those in which hydrogen bonding (base stacking) between the counterpart strands is relatively intact, i.e., is interrupted on average less than one base pair in every 29 consecutive base residues. The term "mis-matched dsRNA" should be understood accordingly.

The dsRNA may be a complex of a polyinosinate and a polycytidylate containing a proportion of uracil bases or guanidine bases, e.g., from 1 in 5 to 1 in 30 such bases (poly I·poly (C4-29×>U or G). The mismatched dsRNA may be poly I·poly C,U in which the ratio of C to U is about 13 to 1 and the sedimentation coefficients of poly I and poly C,U are both less than 9 and within 2 units of each other, that is preferably about 6.5 to 7.5. The dsRNA may be of the general formula $rI_n \cdot (C_{12-13}U)_n$. Other suitable examples of dsRNA are discussed below.

Specific examples of mismatched dsRNA for use in the invention include:

poly (I)·poly ($C_4$,U)
poly (I)·poly ($C_7$, U)
poly (I)·poly ($C_{13}$, U)
poly (I)·poly ($C_{22}$, U)
poly (I)·poly ($C_{20}$, G)
poly (I)·poly ($C_{29}$, G) and
poly (I)·poly ($C_p$) 23 G>p Pharmaceutical compositions in accordance with this invention include the dsRNA, preferably mismatched dsRNA, a lymphokine and, optionally, a compound that inhibits cyclooxygenase activator, as the active components, together with a pharmaceutical carrier or diluent. Pharmaceutical compositions contemplated by this invention include those adapted for parenteral (including subcutaneous, intramuscular, intravenous and intradermal) administration in a suitable pharmaceutical vehicle. Pharmaceutical presentations also include those suitable for rectal, nasal, topical and oral (when suitably protected) administration. When two or more active ingredients are indicated they may be given simultaneously or sequentially.

As used in this specification, the concentration of the dsRNA administered is measured immediately after infusion at a site distal from the point of infusion. Administration by IV drip (400–500 ml) of sterile normal saline containing 200 mg of Ampligen is preferred; however, other modes of administration such as parenterally via intramuscular or subcutaneous injection, intranasally, rectally or orally when suitably protected against the nucleases of the gastrointestinal tract may be considered.

Combination of dsRNAs with other virally-active drugs are also within the scope of this invention, including synergistic combinations of dsRNAs with lymphokines (interferons, interleukins), as my copending application Ser. No. 021,368 filed Mar. 3, 1987, now abandoned, the disclosure of which is hereby incorporated by reference, synergistic combinations of dsRNAs with reverse transcriptase inhibitors (AZT, etc.), lipophiles (amphotericin B, glycoprotein inhibitors (castanospermine) or ribavarin are described in my copending application Ser. No. 028,823 filed Mar. 23, 1987, now abandoned, and 125,097 filed Nov. 25, 1987, now abandoned, the disclosures of both are hereby incorporated by reference.

In addition to the dsRNA, whether or not in combination with another anti-viral drug, a substance which inhibits cyclooxygenase activator may also be administered. As an example of this, the separate or concurrent administration of indomethacin, a prostablandin inhibitor, inhibits prostablandin release and the resultant natural killer (NK) cell down regulation response. The administration of dsRNAs, particularly at more frequent dosage intervals, may be required in instances where the host's natural defence mechanism is seriously impaired. Adminstation of dsRNA may be required on a daily basis. This therapy is enhanced when the natural inhibitors of the desirable MK cells are removed and the NK cell population increased accordingly.

What is claimed:

1. A method of selectively treating an HIV infection or a susceptible viral infection other than HIV which has a common mechanism of viral multiplication or pathogenesis, in whole or in part, similar to that of HIV in a person infected therewith comprising the successive steps of:
   (1) measuring at least one of the person's clinically assessable parameters of the immunological system selected from the group consisting of the T4/T8 cell ratio, a skin sensitivity response to at least one predetermined antigen, and the concentration of HIV in blood or other body fluids or cells and identifying an immune deficit; thereafter
   (2) again measuring the same immune parameter as measured in step (1) at a later time and identifying an immune deficit, and, if the immune deficit measured in step (2) is greater than that measured in step (1),
   (3) instituting therapy with the mismatched dsRNA rIn·r($C_{12,13}$,U)$_n$ in a quantity and for a period of time sufficient to at least stabilize the immune deficit, as compared with the value measured in step (2), thereby at least stabilizing the HIV infection prior to the development of frank acquired immunodeficiency syndrome in that HIV-infected patient.

2. The method of claim 1, in which a plurality of the patient's clinically assessable immune parameters are measured.

3. The method of claim 1, in which the clinically assessable immune parameter having the greatest deficit is measured in step (2).

4. The method of claim 1, in which step (2) is repeated at least once.

5. The method of claim 2, in which the mismatched dsRNA is administered in an amount sufficient to improve the immune deficit measured in step (2).

6. The method of claim 5, in which the quantity and period of administration of the mismatched dsRNA is sufficient to improve the immune deficit measured in steps (1) and (2).

7. The method of claim 1, in which the dsRNA is administered in a range of from 10 mcg/ml blood to 1,000 mcg/ml blood from 1 to 3 times a week.

8. The method of claim 7, in which the dsRNA is administered every other day.

9. The method of claim 7, in which the dsRNA is administered in a range of from about 50 to about 600 mcg/ml blood per day from 1 to 4 times per week.

* * * * *